United States Patent [19]
Shafiee et al.

[11] Patent Number: 5,972,994
[45] Date of Patent: Oct. 26, 1999

[54] MICROBIAL TRANSFORMATION PRODUCTS WITH ANTIFUNGAL PROPERTIES

[75] Inventors: Ali Shafiee, Westfield; Guy H. Harris, Asbury; Deborah L. Zink, Manalapan; Janet M. Sigmund, Cranford; Mark J. Rosenbach, Clark; Suzanne Miller Mandala, Scotch Plains, all of N.J.

[73] Assignee: Merck & Co., Inc., Rahway, N.J.

[21] Appl. No.: 09/047,255

[22] Filed: Mar. 24, 1998

Related U.S. Application Data

[60] Provisional application No. 60/043,316, Apr. 14, 1997.

[51] Int. Cl.⁶ .................... A61K 31/335; C07D 313/00
[52] U.S. Cl. ...................... 514/450; 504/291; 549/271
[58] Field of Search ............... 549/271; 514/450; 504/291

[56] References Cited

FOREIGN PATENT DOCUMENTS 1667724  5/1992  Japan .
1667737  5/1992  Japan .

OTHER PUBLICATIONS

Annals of the NY Academy of Sciences, vol. 544, pp. 128–140 (1988), by H. Achenbach, et al.
J. of Antibiotics, vol. XXXIX, No. 12, pp. 1760–1764 (1986).
J. of Antibiotics, vol. XXXVIII, No. 12, pp. 18061809 (1985).
J. of Antibiotics, vol. XXXVIII, No. 12, pp. 1810–1812 (1985).
J. of Antibiotics, vol. XXXIX, No. 7, pp. 1016–1020 (1986).
Tetrahedron Letters, vol. 26, No. 50, pp. 6167–6170 (1985).

*Primary Examiner*—Amelia Owens
*Attorney, Agent, or Firm*—Elliott Korsen; Mark R. Daniel

[57] ABSTRACT

Biotransformation products of a fermentation with Streptomyces sp., (Merck Culture Collection MA7165) ATCC No. 55946 are potent antifungal agents. These products may be useful in the treatment of diseases caused by fungal pathogens such as Candida sp. and *Cryptococcus neoformans*.

12 Claims, No Drawings

MICROBIAL TRANSFORMATION PRODUCTS WITH ANTIFUNGAL PROPERTIES

This application claims benefit of Provisional Application Ser. No. 60/043,316, filed Apr. 14,1997.

BACKGROUND OF THE INVENTION

The present invention is directed toward the synthesis of novel antifungal agents prepared by biotransformation of known compounds Galbonolide A (Rustmicin) and Galbonolide B.

Galbonolide A (Rustmicin) and Galbonolide B were independently reported in 1985 by Takatoni et al., J. Antibiotics 38, 1807–1809 and Achenbach et al., J. Antibiotics 39, 1760–1764. Galbonolide B was originally isolated as a fungal metabolite from *Micromonospora chalcea* by Otake and from *Streptomyces galbus* by Achenbach, independently. The compounds exhibit antifungal activity against a number of fungi including Candida that is associated with human infections, and *Botrytis cinerea* and *Puccinia graminis* that are associated with plant infections.

Galbonolide B is claimed in Japanese patent JP 1667737 which issued on May 29, 1992. Galbonolide A is claimed in Japanese patent JP 1667724 which also issued on May 29, 1992. No analogs of Galbonolide A or B have been claimed.

Unfortunately, Galbonolide A is chemically unstable. To prepare more stable analogues with potentially useful antifungal activities, a biotransformation process was used to modify known Galbonolides. As a result, two hydroxylated analogues of parent Galbonolides A and B were synthesized.

SUMMARY OF THE INVENTION

The present invention is directed toward the synthesis of novel antifungal compounds of the formula

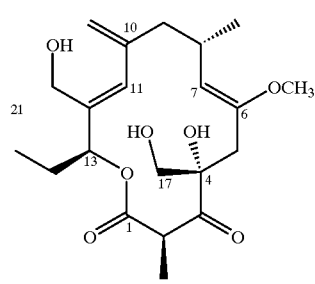

I

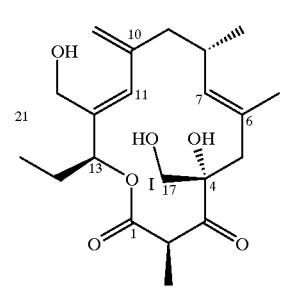

II

These compounds are prepared by biotransformation of Galbonolide A (Rustmicin) and Galbonolide B. These compounds are useful against a number of pathogenic fungi including Candida sp and *Cryptococcus neoformans*.

This invention also relates to processes for the preparation of the compounds by fermentation of *Streptomyces halstedii* MA7165, ATCC NO. 55964 in the presence of the substrate compounds Galbonolide A (Rustmicin) and Galbonolide B.

The invention also relates to pharmaceutical compositions containing a thereapeutically effective amount of either compound I or II in combination with a pharmaceutically acceptable carrier or excipient.

Additionally, the invention relates to a method of treatment of diseases caused by certain fungal pathogens.

DETAILED DESCRIPTION OF THE INVENTION

There are disclosed compounds I and II of the formula

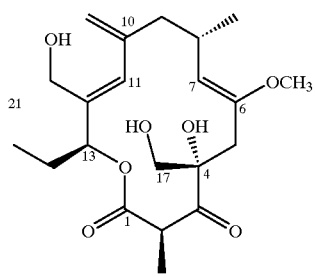

I

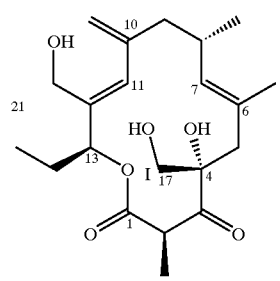

II or a pharmaceutically accepatable salt or hydrate thereof which can be produced by a biotransformation process. The compounds of the present invention are prepared by fermentation of the microorganism *Streptomyces halstedii* MA7165, ATCC No. 55964 in the presence of the substrate compounds, Galbonolide A (Rustmicin) and Galbonolide B, respectively, of the formula:

Galbonolide A

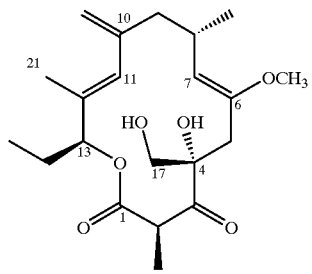

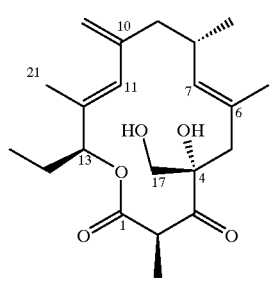

Galbonolide B under appropriate conditions.

A sample of the microorganism *Streptomyces halstedii* has been deposited under the Budapest Treaty in the culture collection of the American Type Culture Collection on Mar. 27, 1997 at 12301 Parklawn Drive, Rockville, Md. 20852 and assigned accession number ATCC 55964.

The following is a general description of MA7165. Observations of growth, general cultural characteristics and carbons source utilization were made in accordance with the methods of Shirling and Gottleib (International J. System. Bacteriol. 16:313–340). Chemical composition of the cells was determined using the methods of Lechevalier and Lechevalier (in Actinomycete Taxonomy, A. Dietz and D. W. Thayer, Ed. Society for Industrial Microbiology, 1980). Coloration of the culture was determined by comparison with color standards in the Inter-Society Council-National Bureau of Standards Centroid Color Charts (US Dept. of Commerce National Bureau of Standards supplement of NBS Circular 553, 1985).

Analysis of Whole Cell Extracts—Peptidoglycan contains LL-diaminopimelic acid.

General growth Characteristics—Good growth on yeast malt extract agar (YME), Glycerol Asparagine agar (GAs), Inorganic Salt Starch agar (ISS) and Oatmeal Agar(Oat). Moderate growth on Czapeks agar and poor growth on water agar supplemented with NZ-Amine A.

Colony Morphology (Oatmeal Agar at 21 days)— Abundance of aerial mycelia that is gray (265.med gy & 266d.gray) and white (263 white) in color. The substrate mycelium is yellow to brown (77.m.ybr) in color. Droplets are present in the aerial mycelium (table 2).

Micromorphology—Aerial mycelia arise from the substrate mycelia and give rise to long flexous spore chains. Sporulation occurs on YME, GAs, ISS, Oatmeal, and Cz agar at 7 days (table 2).

Physiological reactions—The culture produces $H_2S$ on Peptone-yeast-iron agar. Starch is not hydrolyzed and no soluble or melanoid pigments are produced. Carbon source utilization is listed in table 1.

Conclusions—Whole cell analysis reveals that MA7165 has a type I cell wall. Morphological studies reveal that the strain is filamentous and produces flexous aerial spore chains. These are characteristics that are typical of Streptomyces. A comparison of the phenotypic data of MA7165 with that of validly published species of Streptomyces in the taxonomic literature ( Shirling, E. B. and Gottlieb, D., Int. J. Bacteriol.18:69 (1968); Shirling, E. B. and Gottlieb, D., Int. J. Bacteriol.18:279 (1968); Shirling, E. B. and Gottlieb, D., Int. J. Bacteriol.19:391 (1969); Shirling, E. B. and Gottlieb, D., Int. J. Bacteriol.22:265 (1972); Nonomura, H. J. Ferment. Technol. 52:78 (1974); Pridham, T. and Tresner, H., in Bergey's Manual of Determinative Bacteriology, Eight Edition, R. E. Buchanan and N. E. Gibbons, Ed., Williams and Wilkins, Baltiomore (1974) and Loci, R. in Bergy's Manual of Systematic Bacteriology, Vol 4., St. Williams, M. E. Sharpe and J. G. Holt. Ed., Williams and Wilkins, Baltimore. (1989)) indicate that MA7165 bears a strong resemblance to *Streptomyces halstedii*. The only controversial point is that MA7165 utilize mannitol and according to Nonomura, *Streptomyces halstedii* strains do not utilize mannitol. However the current literature shows that 69% of *Streptomyces halstedii* strains utilize mannitol. Therefore, based on the results detailed above it is proposed that MA7165 be classified as a strain of *Streptomyces halstedii*.

TABLE 1

Carbon source utilization of MA7165

| Carbon Source | Utilization |
| --- | --- |
| D-Arabinose | 0 |
| L-Arabinose | 2 |
| D-Fructose | 2 |
| Inositol | 0 |
| alpha D-Lactose | 1 |
| beta D-Lactose | 1 |
| D-Maltose | 2 |
| D-Mannitol | 2 |
| D-Mannose | 2 |
| D-Raffinose | 0 |
| L-Rhamnose | 0 |
| Sucrose | 0 |
| D-Xylose | 2 |
| D-glucose (Positive Control) | 2 |
| Negative Control | 0 |

2 = Good utilization, 1 = Moderate utilization, 0 = Poor to no utilization

TABLE 2

Cultural Characteristics of MA7165 at 21 days

| Medium | Growth | Spore structure | Aerial mycelium color | Reverse Color |
| --- | --- | --- | --- | --- |
| Yeast Malt Extract agar | good | flexous aerial spore chains | gray (265.medgray) white (263 white) | yellow-brown (96d.01Br) |
| Glycerol Asparagine agar | good | flexous aerial spore chains | gray (264.1.gray) white (263.white) | yellow and brown (90gy.y; 96.d.01Br) |
| Inorganic Salt Starch agar | good | flexous aerial spore chains | gray (265.med.gray) white (263.white) | yellow (84.5.Y) |
| Oatmeal agar | good | flexous aerial spore chains | gray (265.med.gray) gray (266.d.gray) white (263.white) | yellow (77.m.yBr) |
| Czapeks agar | moderate | flexous aerial spore chains | gray (264.1.gray) | gray (264.1gray) |

TABLE 2-continued

Cultural Characteristics of MA7165 at 21 days

| Medium | Growth | Spore structure | Aerial mycelium color | Reverse Color |
| --- | --- | --- | --- | --- |
| Water agar | poor | | | |

The present invention can be practiced with any strain of Streptomyces sp. capable of producing compounds I and II. Particularly preferred is the ATCC No. 55964 strain.

In general, compounds I and II may be produced by culturing the above described microorganism in the presence of an appropriate concentration of substrate compounds Galbonolide A and Galbonolide B in an aqueous nutrient medium containing sources of assimilable carbon and nitrogen.

Substrate compounds Galbonolide A and Galbonolide B can be obtained as previously described or by synthetic organic procedures.

The compounds have antimicrobial properties and may be useful for controlling systemic and superficial fungal infections in humans. Additionally, the compounds exhibit activity against certain plant fungal pathogens and may be useful as a broad spectrum crop antifungal agent.

The compounds of this invention have antimicrobial properties and are especially useful as antifungal agents against yeasts. They are useful against organisms causing systemic human pathogenic mycotic infections such as Candida sp. and *Cryptococcus neoformans*. These properties may be effectively utilized by administering compositions containing an antifungal amount of the compound to an area, object or subject, on or in which fungi are to be controlled. Thus, compositions containing an antifungally effective amount of the compounds and their use for the control of fungi are aspects of the present invention. An especially preferred aspect of the present invention are compositions in a pharmaceutically acceptable carrier and their use for the control of mycotic infections by administering a therapeutically effective amount of the compounds.

Compounds I and II may be useful as antifungal agents, especially as antimycotic agents, which may be demonstrated with the compounds in a broth microdilution assay for the determination of minimum inhibitory concentration (MIC). The compounds are found to be effective in the assay against fungi selected for their resistance/susceptibility to known compounds, animal virulence, source and clinical importance, at concentrations comparable to an established antifungal agent, amphotericin B.

In the microbroth dilution assay, microorganisms were selected by inoculating 5 milliliters of YNBD broth (yeast nitrogen base with 2% dextrose; Difco) with 50 microliters of yeast culture stored as a 20% glycerol stock at −76° C., or by streaking a yeast culture on Sabouraud dextrose agar (SDA) and incubating for 24–48 hours at 35–37° C. Three to five characteristic colonies were selected and transferred to a fresh plate and incubated under similar conditions. From the regrowth, 3 to 5 colonies were selected and suspended in 5 milliliters of YNBD broth. The liquid cultures were incubated for 16 hours at 35–37° C. in a rollerdrum turning at 56 rpm. The 16 hour broth cultures were adjusted optically to $OD_{600}$ of 0.01 by dilution in YNBD and incubated for 5 hours at 35–37° C. in a rollerdrum turning at 56 rpm. The cultures were further diluted in YNBD to $OD_{600}$ of 0.0014, resulting in a concentration of $1-5\times10^4$ cfu/ml which was used as inocula.

The test compound was dissolved at 128 μg/ml in 20% methanol and diluted two-fold in YNBD to achieve a concentration of 64 μg/ml at 10% methanol in the first well of a 96-well, U-bottomed plate. Compounds in column 1 were subsequently serially diluted two-fold and 75 μl of cell suspension was added to each well resulting in an additional two-fold dilution of compound to yield concentrations from 32 μg/ml to 0.0075 μg/ml.

Galbonolide A, the control compound, was prepared as described above for Compound I.

The plates containing the diluted compounds and cell inocula were incubated for 48 hours at 35–37° C. with MIC (minimum inhibitory concentration) determinations carried out after 24 hours and 48 hours of incubation. Growth and sterility controls for each organism and sterility checks for the compounds also were carried out.

| | Compound I | |
| --- | --- | --- |
| | MIC24 | MIC48 |
| C. albicans | 32 | >32 |
| C. neoformans (2061) | 0.125 | 0.25 |
| C. neoformans (2062) | 0.125 | 0.25 |

In view of the potent activity, the compound of the present invention, either singly or as a mixture, is adaptable to being utilized in various applications of antifungal compositions. In such case, compounds may be admixed with a biologically inert carrier, generally with the aid of a surface active dispersing agent, the nature of which would vary depending on whether the use is for the control of pathogens infecting man or animals, or for control of fungi in agriculture such as in soil or plant parts, or for the control of fungi in inanimate objects.

In compositions for medical applications, the compound may be admixed with a pharmaceutically acceptable carrier, the nature of which will depend on whether the composition is to be topical, parenteral or oral.

If said application is to be topical, the drug may be formulated in conventional creams and ointments such as white petrolatum, anhydrous lanolin, cetyl alcohol, cold cream, glyceryl monostearate, rose water and the like.

For parenteral applications, the compounds may be formulated in conventional parenteral solutions such as 0.85 percent sodium chloride or 5 percent dextrose in water, or other pharmaceutically acceptable compositions.

Compositions for oral administration may be prepared by mixing the component drugs with any of the usual pharmaceutical media, including for liquid preparations, liquid carriers such as water, glycols, oils, alcohols, and the like; and for solid preparations such as capsules and tablets, solid carriers such as starches, sugars, kaolin, ethyl cellulose, surface active dispersing agents, generally with lubricants such as calcium stearate, together with binders, disintegrating agents and the like. Water is the preferred liquid carrier for the compound of the invention.

These compositions are then administered in amounts sufficient to obtain the desired antifungal effect. For medical applications, the method comprises administering to a subject in need of treatment a therapeutically effective antifungal amount of the compounds. The appropriate dose will vary depending on age, severity, body weight and other conditions. For topical application, the compositions are applied directly to the area where control is desired. For internal administration, the composition may be applied by injection or may be administered orally.

For non-medical application, the product of the present invention, either alone or as a mixture, may be employed in compositions in an inert carrier which included finely divided dry or liquid diluents, extenders, fillers, conditioners and excipients, including various clays, diatomaceous earth, talc, and the like or water and various organic liquids such as lower alkanols, such as ethanol and isopropanol.

Compositions for injection, a preferred route of delivery, may be prepared in unit dosage form in ampules, or in multidose containers. The injectable compositions may take such forms as suspensions, solutions, or emulsions in oily or aqueous vehicles, and may contain various formulating agents. Alternatively, the active ingredient may be in powder (lyophillized or non-lyophillized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Topical applications may be formulated in carriers such as hydrophobic or hydrophilic bases to form ointments, creams, lotions, in aqueous, oleaginous or alcoholic liquids to form paints or in dry diluents to form powders.

Oral compositions may take such forms as tablets, capsules, oral suspensions and oral solutions. The oral composions may utilize carriers such as conventional formulating agents, and may include sustained release properties as well as rapid delivery forms.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the antibacterial arts. Another factor influencing the precise dosage regimen, apart from the nature of the infection and peculiar identity of the individual being treated, is the molecular weight of the compound.

The compositions for human delivery per unit dosage, whether liquid or solid, may contain from about 0.01% to as high as about 99% of active material, the preferred range being from about 10–60%. The composition will generally contain from about 15 mg to about 2.5 g of the active ingredient; however, in general, it is preferable to employ dosage amounts in the range of from about 250 mg to 1000 mg. In parenteral administration, the unit dosage will typically include the pure compound in sterile water solution or in the form of a soluble powder intended for solution, which can be adjusted to neutral pH and isotonic.

The preferred methods of administration of the antifungal compounds include oral and parenteral, e.g., i.v. infusion, i.v. bolus and i.m. injection.

The following examples are provided for the purpose of illustrating the present invention and shall not be construed as limiting the scope or spirit of the invention.

EXAMPLE 1

Biotransformation of Galbonolide A a. Preparation of Biotransformation Cultures

Cultures under investigation were grown under our standard conditions in seed and biotransformation media, respectively. Seed consisted of: 0.1% dextrose, 1% dextrin, 0.3% beef extract, 0.5% ardamine pH, 0.5% NZ amine type E, 0.005% $MgSO_4$ $7H_2O$, 0.037% $K_2HPO_4$, and 0.05% $CaCO_3$ with pH adjusted to 7.1 before autoclaving. Biotransformation medium contained: 2% glucose, 0.5% soya meal, 0.5% yeast extract, 0.5% NaCl, 0.98% MES with pH adjusted to 7.0 before autoclaving.

b. Preparation of Resting Cells

Frozen seed cultures or isolated colonies stored on solid agar plates were used for inoculation of the seed medium. Usually, two milliliters of seed or loopfuls of culture were inoculated into a 250 ml plain Erlenmeyer flask containing 50 ml of the seed medium. These cultures were incubated at 27° C. on a shaker with 220 rpm gyratory agitation. After 40 hrs of incubation, 2 ml of the seed culture was transferred into 50 ml of the biotransformation medium in a 250 ml baffled Erlenmyer flask. Incubation continued for 40 hrs under the same conditions as described above for the seed cultures. The biotransformation cultures were harvested by centrifugation on a Beckman table top centrifuge at 3750 rpm for 15 min. The pellet was then washed three times by suspension into 0.1 M MES buffer, pH 5.5, followed by centrifugation. The wash pellet was then used for biotransformation or stored at –80° C. for the future use.

c. Biotransformation Procedure

Ten grams (wet weight) of washed cells prepared from each screening culture was suspended in 0.1 M MES buffer, pH 5.5, and the final volume was brought to 30 ml. One milligram of Galbonolide A, dissolved in 0.1 ml of methanol, was added to each flask containing cell suspension and the flasks were incubated under the above described conditions. At different time intervals, a sample was withdrawn from each flask and mixed with equal volumes of methanol. After vortexing the sample was centrifuged and the supernatant was recovered. An aliquot of the resulting supernatant was then analyzed for the formation of new product by HPLC using a reverse-phase C18 column.

d. Isolation and Characterization of the Product

The biotransformation culture was extracted with an equal volume of methanol. This solution was twice extracted with heptane (15 mL). The aqueous layer was then diluted with $H_2O$ (15 mL) and extracted with $CH_2Cl_2$ (15 mL). The $CH_2Cl_2$ layer was washed with $H_2O$, brine, dried over anhydrous $Na_2SO_4$ and concentrated in vacuo to dryness. Compound I was purified from the $CH_2Cl_2$ extract using RP HPLC on Phenomenex Primesphere C8 with mobile phase consisting of 60% MeOH/40% 0.025 M $NH_4OAc$ pH 4.5, a flow rate of 1.0 mL/min at 40° C. and 0.5 min. fractions were collected. The fractions containing Compound I were combined and extracted with $CH_2Cl_2$, the $CH_2Cl_2$ layer washed with $H_2O$, brine, dried over anhydrous $Na_2SO_4$ and concentrated under $N_2$ to yield 1.56 mg of compound I.

Mass spectra were recorded on Jeol SX-102A (electron impact, EI,90 eV) and TSQ700 (LC-MS-ESI, Liquid chromatography-Electrospray ionization) mass spectrometers. Exact mass measurements were performed at high resolution (HR-EI) using perfluorokerosene (PFK) as an internal standard. The molecular ion of compound I was observed at m/z 380. Scanning high resolution EI mass measurements suggested a molecular formula of $C_{21}H_{32}O_6$; found 380.2187, calculated 380.2199.

$^1H$ and $^{13}C$ NMR spectra were recorded at 500 MHz or 125 MHz respectively at 25° C. on a Varian Unity 500 spectrometer equipped with a Nalorac micro-inverse detection probe. Chemical shifts are reported in ppm downfield from TMS (tetramethylsilane) and spectra were refereneced to the solvent peak (7.15 ppm). $^1$H NMR Compound I in 125 µl $C_6D_6$: δ 0.837 (t, 7.0, 3H, H-15), 0.908 (d, 7.0, 3H, H-19), 1.382 (d, 7.0, 3H, H-16), 1.67 (m, 2H, H-14), 1.840 (dd, 3.0, 11.2, C-17 OH), 1.939 (brt, 5.2, C-21 OH), 2.112 (dd, 2.9, 13.2, 1H, H-9a), 2.274 (d, 14.9, 1H, H-5a), 2.354 (dd, 7.7, 13.2, 1H, H-9b), 2.485 (d, 14.9, 1H, H-5b), 2.93 (m, 1H, H-8), 3.172 (s, 3H, H-18), 3.342 (dd, 3.1, 11.9, 1H, H-17a), 3.572 (dt, <1, 12.0, 1H, H-17b), 3.713 (q, 7.0, 1H, H-2), 3.822 (s, C-4 OH), 4.126 (dd, 4.9, 12.7, 1H, H-21a), 4.488 (dd, 4.4, 12.6, 1H, H-21b), 4.671 (d, 9.4, 1H, H-7), 4.829 (brs, 1H, H-20a), 4.908 (brs, 1H, H-20b), 5.226 (t, 7.3, 1H, H-13), 6.117 (brs, 1H, H-11).

EXAMPLE 2

Biotransformation of Galbonolide B a. Preparation of Biotransformation Cultures

Screening cultures under investigation were grown under our standard conditions in seed and biotransformation media, respectively. Seed medium consisted of: 0.1% dextrose, 1% dextrin, 0.3% beef extract, 0.5% ardamine pH, 0.5% NZ amine type E, 0.005% $MgSO_4$ $7H_2O$, 0.037% $K_2HPO_4$, and 0.05% $CaCO_3$ with pH adjusted to 7.1 before autoclaving. Biotransformation medium contained: 2% glucose, 0.5% soya meal, 0.5% yeast extract, 0.5% NaCl, 0.98% MES with pH adjusted to 7.0 before autoclaving.

b. Preparation of Resting Cells

Frozen seed cultures or isolated colonies stored on solid agar plates were used for inoculation of the seeed medium. Usually, two milliliters of seed or a loopful of culture were inoculated into a 250 ml plain Erlenmeyer flask containing 50 ml of the seed medium. These cultures were incubated at 27° C. on a shaker with 220 rpm gyratory agitation. After 40 hrs of incubation, 2 ml of the seed culture was transferred into 50 ml of the biotransformation medium in a 250 ml baffled Erlenmeyer flask and incubation continued for 40 hrs under the same conditions as described above for the seed cultures. The biotransformation cultures were harvested by centrifugation on a Beckman table top centrifuge at 3750 rpm for 15 min. The pellet was then washed three times by suspension into 0.1 M MES buffer, pH 5.5, followed by centrifugation. The washed pellet was then used for biotransformation or stored at −80° C. for the future use.

c. Biotransformation Procedure

Ten grams (wet weight) of washed cells prepared from each screening culture was suspended in 0.1 M MES buffer, pH 5.5, and the final volume was brought to 30 ml. One milligram of compound Galbonolide B dissolved in 0.1 ml of methanol, was added to each flask containing cell suspension and the flasks were incubated under the above-described conditions. At different time intervals, a sample was withdrawn from each flask and mixed with equal volumes of methanol. After vortexing, the sample was centrifuged and the supernatant was recovered. An aliquot of the resulting supernatant was then analysed for the formation of a new product by HPLC using a reverse-phase C18 column.

d. Isolation and Characterization of the Product

The biotransformation culture was extracted and purified from the $CH_2Cl_2$ extract prepared as described for Compound I except a mobile phase consisting of 72% MeOH/ 28% 0.025 M $NH_4OAc$ at pH 4.5 was used.

$^1$H NMR for Compound II in 125 µl $C_6D_6$: δ 0.844 (d, 6.5), 0.858 (t, 7.5), 1.408 (d, 7.0), 1.639 (br s), 1.680 (m), 1.852 (d, 14), 2.110 (dd, 7.5, 13), 2.198 (br d, 12), 2.43 (m), 2.674 (d, 14), 3.276 (d, 11.5), 3.468 (br t, 10.5), 3.776 (dq, 6.5), 4.102 (d, 12.5), 4.558 (d, 12.5), 4.805 (br s), 4.925, br s), 5.166 (br d, 9.5), 5.230 (br t, 7.0), 6.117 (br s). $^{13}$C NMR for Compound II in 125 µl $C_6D_6$: δ 10.3, 15.4, 19.10, 19.37, 27.8, 33.0, 41.0, 45.0, 49.4, 60.567.8, 78.5, 84.5, 118.4, 128.2 (obscured by solvent), 131.0, 136.3, 139.8, 143.3, 169.1, 208.5.

Mass spectra were recorded on Jeol SX-102A (electron impact, EI,90 eV) and TSQ700 (LC-MS-ESI, Liquid chromatography-Electrospray ionization) mass spectrometers. Exact mass measurements were performed at high resolution (HR-EI) using perfluorokerosene (PFK) as an internal standard. The molecular ion of compound II was observed by ESI as the Na adduct at m/z 419 (396 (M) +Na). High resolution EI-MS data was obtained on M-$H_2O$ observed at m/z 378. The empirical formula obtained for this ion is $C_{21}H_{30}O_6$; found 378.2028, calculated 378.2042, for $C_{21}H_{32}O_7$—$H_2O$. This corresponds to a molecular formula of $C_{21}H_{32}O_7$.

The following examples illustrate representative compositions containing Compound I or II.

EXAMPLE A 1000 compressed tablets each containing 500 milligrams of Compound I are prepared from the following formulation:

|  | Grams |
| --- | --- |
| Compound I | 500 |
| Starch | 750 |
| Dibasic calcium phosphate hydrous | 5000 |
| Calcium stearate | 2.5 |

The finely powdered ingredients are mixed well and granulated with 10 percent starch paste. The granulation is dried and compressed into tablets.

EXAMPLE B 1000 hard gelatin capsules, each containing 500 milligrams of Compound I are prepared from the following formulation:

| Compound I | 500 |
| --- | --- |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE C 250 milliliters of an injectible solution are prepared by conventional procedures from the following formulation:

| Dextrose | 12.5 grams |
| --- | --- |
| Water | 250 milliliters |
| Compound I | 400 milligrams |

The ingredients are blended and sterilized for use.

EXAMPLE D

An ointment suitable for topical application may be prepared by intimately dispersing 13 mg of Compound I in 1 g of commercially available polyethylene/hydrocarbon gel.

EXAMPLE E

An aerosol composition may be prepared having the following formulation (per canister):

| | |
|---|---|
| Compound I | 24 mg |
| Lecithin NF, liquid concentrate | 1.2 mg |
| Trichlorofluoromethane | 4.025 g |
| Dichlorodefluoromethane | 12.15 g |

While the foregoing specification teaches the principles of the present invention, it will be understood that the practice of the invention encompasses all of the casual variations, adaptations, modifications, deletions, or additions of procedures and protocols described herein, as come within the scope of the following claims and its equivalents.

What is claimed is:

1. A compound of the formula

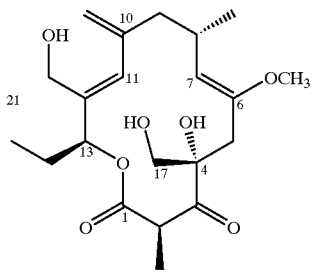

I

2. A compound of the formula

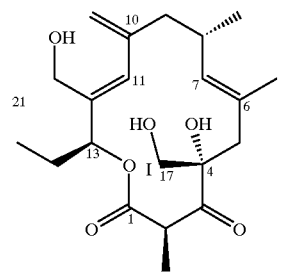

II

3. A process for the preparation of the compound of claim 1 which comprises a. contacting a compound of the formula

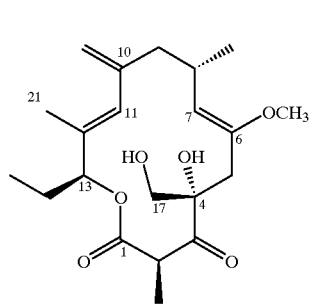

Galbonolide A with *Streptomyces halstedii* MA7165, ATCC 55946; and
b. isolating the compound of claim 1.

4. A process for the preparation of the compound of claim 2 which comprises a. contacting a compound of the formula

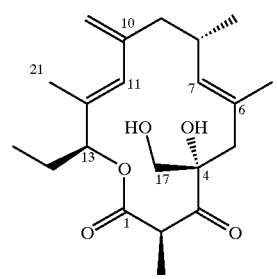

Galbonolide B with *Streptomyces halstedii* MA7165, ATCC 55946; and
b. isolating the compound of claim 2.

5. An antifungal composition comprising an antifungal amount of the compound of claim 1 and a biologically inert carrier or diluent therefor.

6. The composition according to claim 5 wherein the carrier is a pharmaceutically acceptable carrier.

7. An antifungal composition comprising an antifungal amount of the compound of claim 2 and a biologically inert carrier or diluent therefor.

8. The composition according to claim 7 wherein the carrier is a pharmaceutically acceptable carrier.

9. A method of treating fungal infections in mammals comprising administering to a patient in need thereof an antifungally effective amount of the compound of claim 1.

10. A method of treating fungal infections in mammals comprising administering to a patient in need thereof an antifungally effective amount of the compound of claim 2.

11. A method for treating agricultural fungal infections which comprises administering to the site where growth is to be treated an effective amount of the compound of claim 1.

12. A method for treating agricultural fungal infections which comprises administering to the site where growth is to be treated an effective amount of the compound of claim 2.

* * * * *